United States Patent [19]

Sak

[11] Patent Number: 5,787,891

[45] Date of Patent: Aug. 4, 1998

[54] METHOD AND APPARATUS FOR SAMPLING CERVICAL TISSUE

[76] Inventor: Robert Sak, 9674 Colorado Ct., Boca Raton, Fla. 33434

[21] Appl. No.: 405,205

[22] Filed: Mar. 16, 1995

[51] Int. Cl.⁶ .................................................. A61B 10/00
[52] U.S. Cl. .................................... 128/756; 128/159
[58] Field of Search .................................. 128/749, 750, 128/754, 755, 756, 757, 758, 759, 778, 840; 604/55

[56] References Cited

U.S. PATENT DOCUMENTS

| | | | |
|---|---|---|---|
| 2,767,703 | 10/1956 | Nieburgs | 128/749 |
| 3,776,219 | 12/1973 | Brown | 128/759 |
| 3,995,618 | 12/1976 | Kingsley et al. | 128/759 |
| 4,157,709 | 6/1979 | Schuster et al. | 128/759 |
| 4,586,601 | 5/1986 | Alter | 128/756 |
| 4,628,941 | 12/1986 | Kosasky | 128/759 |
| 4,784,158 | 11/1988 | Okimoto | 128/759 |
| 4,788,985 | 12/1988 | Manning et al. | 128/759 |
| 4,862,899 | 9/1989 | Bucaro | 128/749 |
| 4,877,037 | 10/1989 | Ko et al. | 128/759 |
| 5,121,752 | 6/1992 | Canna | 128/759 |
| 5,449,071 | 9/1995 | Levy | 206/569 |

*Primary Examiner*—Max Hindenburg
*Assistant Examiner*—Pamela L. Wingood
*Attorney, Agent, or Firm*—Banner & Witcoff, Ltd.

[57] ABSTRACT

A cervical sampling system includes a vaginal insert tube, a removable swab sleeve, a sampling swab, and a stem for pushing the swab into contact with the cervical tissue. A kit using the sampling system for in-home Pap smear tests is also disclosed.

20 Claims, 4 Drawing Sheets

METHOD AND APPARATUS FOR SAMPLING CERVICAL TISSUE

BACKGROUND OF THE INVENTION

The present invention relates to an apparatus for obtaining a sample of cervical tissue and/or vaginal secretions such that developing cancerous cells may be detected. The present invention also relates to a method of using the sampling apparatus in a home administered Pap smear test kit.

SUMMARY OF THE INVENTION

The early detection of cervical, uterine and vaginal cancer is paramount to the effective treatment and recovery from the disease. A Papanicolaou smear test, commonly referred to as a Pap test, has long been established as a highly useful diagnostic tool which allows the identification of premalignant and malignant tissue at very early stages of the disease, as well as the identification of various inflammations and infections. A Pap test is a clinical procedure in which a speculum is inserted into the vagina and the cervix is exposed. A sample smear of cervical or vaginal secretions are then removed with a scraper, probe, brush or similar type of device. The collected smear is then placed upon microscopic slides and examined for exfoliated cells. The cells are examined for the early detection of cancer or to determine the presence of certain hormonal conditions or certain infections.

Despite their broad diagnostic effectiveness for the early detection of cancer, Pap smear tests are performed almost exclusively by trained medical personnel, such as the gynecologist or internist, due to the complicity of the equipment. The natural reluctance of female patients to visit the gynecologist for such an intrusive procedure coupled with the financial burden of the doctor's bill and the time constraints of the work week, results in many women not receiving a Pap test examination as frequently as advised by the American Cancer Society, or even worse, not at all.

Cervical sampling systems designed for self administration have been proposed, e.g. in U.S. Pat. Nos. 5,121,752 (Canna), 4,862,899 (Bucaro), 4,788,985 (Manng et al.), 4,157,709 (Shuster et al.), 3,995,618 (Kingsley et al.), and 3,776,219 (Brown). These prior art systems, however, fall short of that required for dependable at home use, both in ease of use and in cost. The methodology for use is inordinately complicated and extremely difficult to use to obtain reliable samples needed for testing. Prior art systems also require expensive manufacturing procedures which thereby negate their commercial viability. Thus, cost, inconvenience, and embarrassment involved with a doctor's office visit results in an inordinate number of women who do not avail themselves of the availability of early detection and treatment of cancer.

SUMMARY OF THE PRESENT INVENTION

The present invention overcomes the disadvantages of the prior art by providing a cervical sampling device that is simple to use and relatively inexpensive to manufacture. The cervical sampling device includes a vaginal insert tube, a guide sleeve located within the vaginal insert tube, and a swab assembly removably disposed within the guide tube. The swab assembly includes a swab sleeve and a swab disposed therein for obtaining a cervical sample. The swab is positioned within the swab sleeve in a retracted position when first inserted into the vaginal cavity. A stem is then used for pushing the swab out of the swab sleeve to an extended position and into contact with cervical tissue. A second swab sleeve and a second swab may also be used with the cervical sampling device of the present invention.

The methodology of using the present invention includes inserting the vaginal insert tube, with the first swab assembly therein, into a vaginal cavity. Pressure is then applied to the first stem to extend the first swab from the retracted position within the first swab sleeve into the extended position and into contact with cervical tissue. The first cervical tissue sample is thereby absorbed into the first swab and the first stem is thereafter withdrawn in order to retract the first swab back into the first swab sleeve. The first swab assembly may then be removed from the vaginal insert tube while maintaining the position of the vaginal insert tube within the vagina. Thus, the second swab assembly can then be inserted into the already in place vaginal insert tube. Pressure is similarly applied to the second stem to extend the second swab from the retracted position within the second swab sleeve into the extended position and into contact with cervical tissue. The second cervical tissue sample is thereby absorbed into the second swab and the second stem is thereafter withdrawn in order to retract the second swab back into the second swab sleeve. The second swab assembly may then be removed from the vaginal insert tube or the vaginal insert tube itself may be removed. Once completed with the sampling procedures, the first and second cervical tissue samples are fixed onto first and second slides and forwarded to an appropriate facility for analysis.

The present invention also relates to a Pap smear test system in kit form. The system includes the cervical sampling device, the second swab assembly, slides for receiving the cervical tissue samples, and one or more packages for mailing the slides to a laboratory or other facility for analysis. The inclusive feature of the system is that all of the elements of the kit may be contained within one convenient package.

Other objects, features and advantages of the present invention will be apparent from the following detailed description and drawings.

DETAILED DESCRIPTION OF THE PREFERRED EMBODIMENTS

Figure 1:
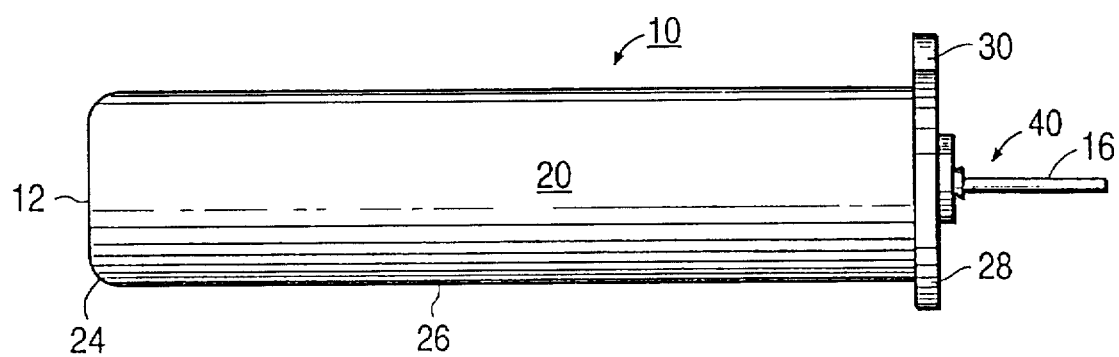
FIG. 1 is a side view of a sampling device constructed in accordance with a preferred embodiment of the present invention.
Figure 2:
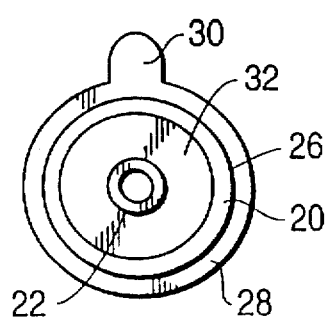
FIG. 2 is a partial front end view of the sampling device of FIG. 1, showing the insert tube, a first spacer, and the guide sleeve.
Figure 3:
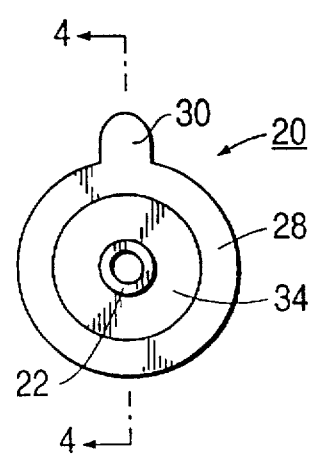
FIG. 3 is a partial rear end view of the sampling device of FIG. 1, showing the insert tube, a second spacer, and the guide sleeve.
Figure 4:
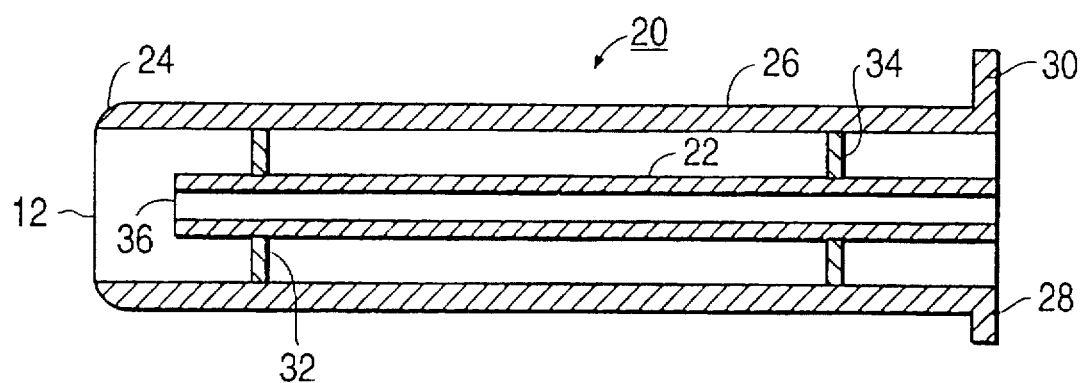
FIG. 4 is a partial cross-sectional view taken along the line 4—4 of FIG. 3, showing the vaginal insert and guide sleeve for the sampling device of FIG. 1.

Referring now to the drawings, where like references to numerals indicate like elements, there is shown in FIG. 1 a cervical sampling device (10) constructed in accordance with a preferred embodiment of the present invention. As illustrated in FIGS. 1–4, the device (10) is preferably formed of a vaginal insert tube (20) and an inner tubular guide sleeve (22). The front end (12) of the insert tube (20) is tapered (24) in order to facilitate insertion into the vaginal canal, as discussed further below. The tube (20) has a cylindrical outer periphery (26) and a radially extending flange (28) located towards the rear end thereof. A handle (30) for manipulating and removing the tube (20) may also be formed integral with the flange (28).

In a preferred embodiment of the invention, the tube (20) is approximately 5.5 inches long (approximately 14 centimeters), such that the flange (28) stops the front end (12) of tube (20) immediately in front of the cervix. The tube (20) has a cylindrical periphery (26) with an outer diameter of approximately 1.125 inches (approximately 3 centimeters) in order to comfortably fit within the vaginal canal. The tubular guide (22) is rigidly supported within the insert tube (20) by annular spacers (32, 34). As shown, the tubular guide (22) is preferably shorter than the insert tube (20). Locating the front end (36) of the guide tube (22) behind the front end (12) of the insert tube (20) is advantageous in terms of directing the swab (14) to the desired position for sampling, as discussed further below. In the preferred embodiment, the distance between the front end (36) of the tubular guide (22) and the front end (12) of the insert tube (20) is approximately 0.5 inch, (approximately 1.5 centimeters) which allows the brush portion of the swab (14) to expand or open before coming into contact with the cervix.

The insert tube (20), the guide sleeve (22) and the spacers (32, 34) may be formed of transparent plastic. Transparent material makes it easier for the user to understand how the sampling device (10) operates, which is an important consideration since the device (10) may be used by a woman with no medical training. The plastic material for the device (10) should preferably be lightweight, relatively inexpensive, sterilizable, and inert.

Figure 5:
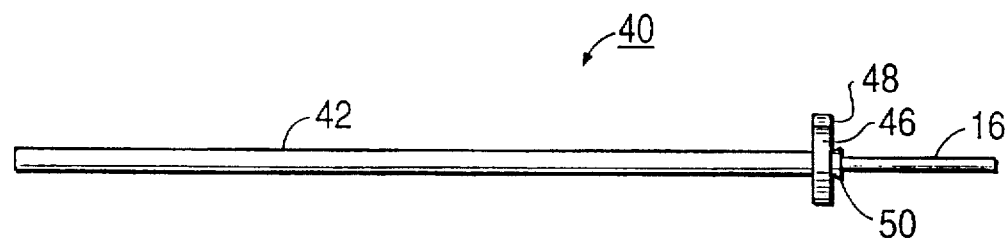
FIG. 5 is a side view of a swab sleeve assembly for the sampling device of FIG. 1.
Figure 6:
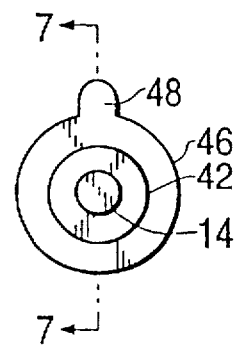
FIG. 6 is a front end view of the swab sleeve assembly of FIG. 5.
Figure 7:
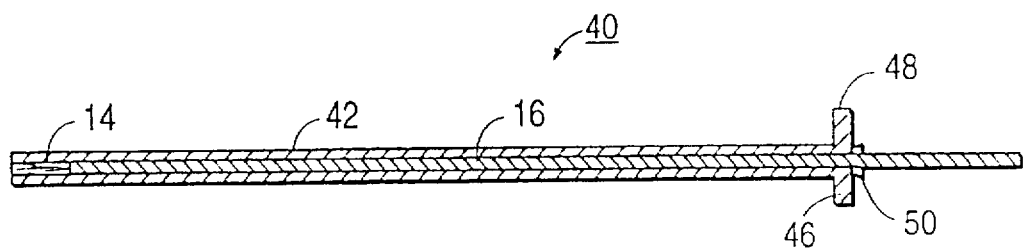
FIG. 7 is a cross-sectional view of the swab sleeve assembly of FIG. 5, taken along the line 7—7 of FIG. 6.

A swab sleeve assembly (40) constructed in accordance with the present invention is illustrated in FIGS. 5–7. The swab sleeve assembly (40) includes a swab sleeve (42), the absorbent swab (14) and the stem (16). The stem (16) is integrally connected to the swab (14) such that the swab (14) and the stem (16) slide together through the swab sleeve (42). The outer diameter of the swab sleeve (42) is approximately the same as the inner diameter of the guide sleeve (22), such that the swab sleeve (42) slides smoothly within and is guided by the guide sleeve (22). A radially extending flange (46) is provided at the rear end of the swab sleeve (42). The flange (46) prevents the swab sleeve (42) from sliding too far into the guide sleeve (22). A handle (48) is formed integral with the flange (46). The handle (48) is used to slide the swab sleeve (42) into and out of the guide sleeve (22), and to align the stem (16) as discussed in more detail below. In an alternative embodiment of the invention, swab sleeve assembly (40) is inserted directly within insert tube (20) and the use of guide sleeve (22) is thereby omitted.

In a preferred embodiment, the swab sleeve (42) may advantageously be formed of the same transparent plastic material as that of the insert tube (20). The swab (14) may be formed of a suitable absorbent material, such as sterile cotton intertwined with a soft bristle, for example. Swab (14) may also include any type of swab, brush, scraper, probe or the like which can similarly be used to collect a cell specimen. Preferably, swab (14) is in a collapsed or closed position when contained within swab sleeve (42) and then expands or opens when pushed out of swab sleeve (42) by stem (16). The stem (16) is preferably formed of a resilient plastic material and has a resilient collar (50) for initially stopping the stem (16) from moving into the swab sleeve (42) (to the left as viewed in FIG. 7) beyond the stored position shown in FIG. 7. The collar (50) also functions to align the stem (16) with respect to the swab sleeve (42) so that the swab (14) will be properly aligned with the handle (48) during sampling, as discussed in more detail below. The stem (16) should be long enough to be grasped by the user's fingers when the swab (14) is in the sampling position shown in FIG. 8.

Briefly, the sampling device in accordance with the present invention is used in the following manner. The device (10) is positioned within the vagina with its front end (12) located immediately in front of the cervix. Swab (14) is then pushed into contact with the cervix by a stem (16), and a cervical tissue sample is absorbed by the swab (14). The swab (14) is then removed from the vagina, the sample is transferred from the swab (14) to a slide (18) and a fixing medium (58) is applied. The slide (18) is then packaged and sent to a laboratory for analysis.

In a more detailed explanation of the operation, the device (10) is first provided in the position shown in FIG. 7, with the swab (14) held within the swab sleeve (42) by the stop collar (50), and with the rear flange (46) of the swab sleeve (42) in contact with the rear end of the guide sleeve (22). The device (10) is then positioned within the vagina. The tapered front end (12) and the rear flange (28) are configured such that the initial positioning of the device (10) can be accomplished reliably and accurately by an in-home user with no medical training.

Figure 8:
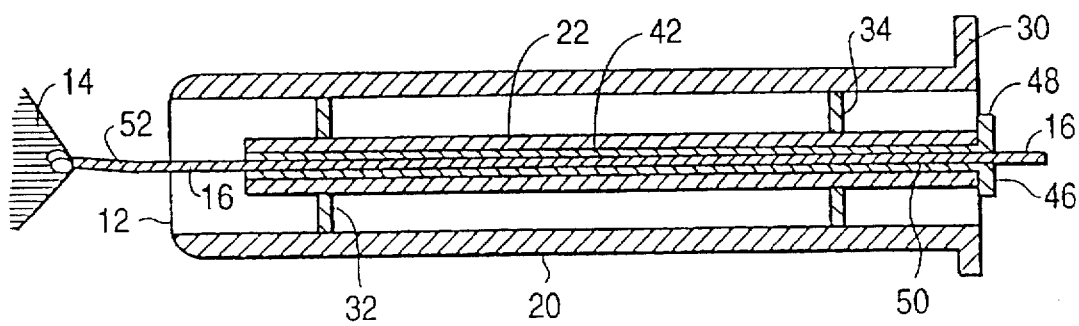
FIG. 8 is a cross-sectional view similar to that of FIG. 4, showing the sampling device of FIG. 1 with a swab in an extended position.

Once the tube (20) is in its fully inserted position the stem (16) is pushed forwardly to the sampling position shown in FIG. 8. The resiliency of the collar (50) is easily overcome in this step since only a relatively small amount of force is needed to push the collar (50) into the swab sleeve (42). As the swab (14) leaves the swab sleeve (42) the stem (16) bends upwardly (as shown by reference numeral 52) to form an angle of about five degrees. The resilient bending of the stem (16) moves the swab (14) into the preferred position for obtaining the desired cervical sample. In the illustrated embodiment of the invention, the distance between the front end of the swab (14) and the bend in the stem (shown by reference numeral (52)) is approximately 1.0 inch (approximately 2.5 centimeters). The swab sleeve (42) has an offset portion or handle (48) to allow for the centering of the swab in position around the cervix for accurate tissue sampling. Accordingly, the swab (14) is positioned in the proper orientation (bent upwardly) when the handle (48) is in the upright position or extending upwardly as shown in FIGS. 5–7. Thus, the handle (48) acts as a means for properly aligning the stem (16) and the swab (14) after they are inserted within the vagina.

After the sample has been absorbed into the swab (14) or otherwise collected, the stem (16) is pulled rearwardly (to the right as viewed in FIG. 8) until the collar (50) comes out of the swab sleeve (42). The stem (16) may be formed of resilient plastic material such that when the stem (16) is retracted into the swab (42), the stem (16) becomes realigned with the axis of the swab sleeve (42). When the stem (16) is fully retracted, the swab sleeve assembly (40)

is again in the position shown in FIGS. 5–7. In this retracted position, the swab is protected within the swab sleeve (42). The swab sleeve assembly (40) may then removed from the vaginal insert tube (20), leaving the tube (20) within the vagina in order to obtain a second sampling as discussed below, or the entire sampling device (10) may be removed from the vagina.

Figure 9:
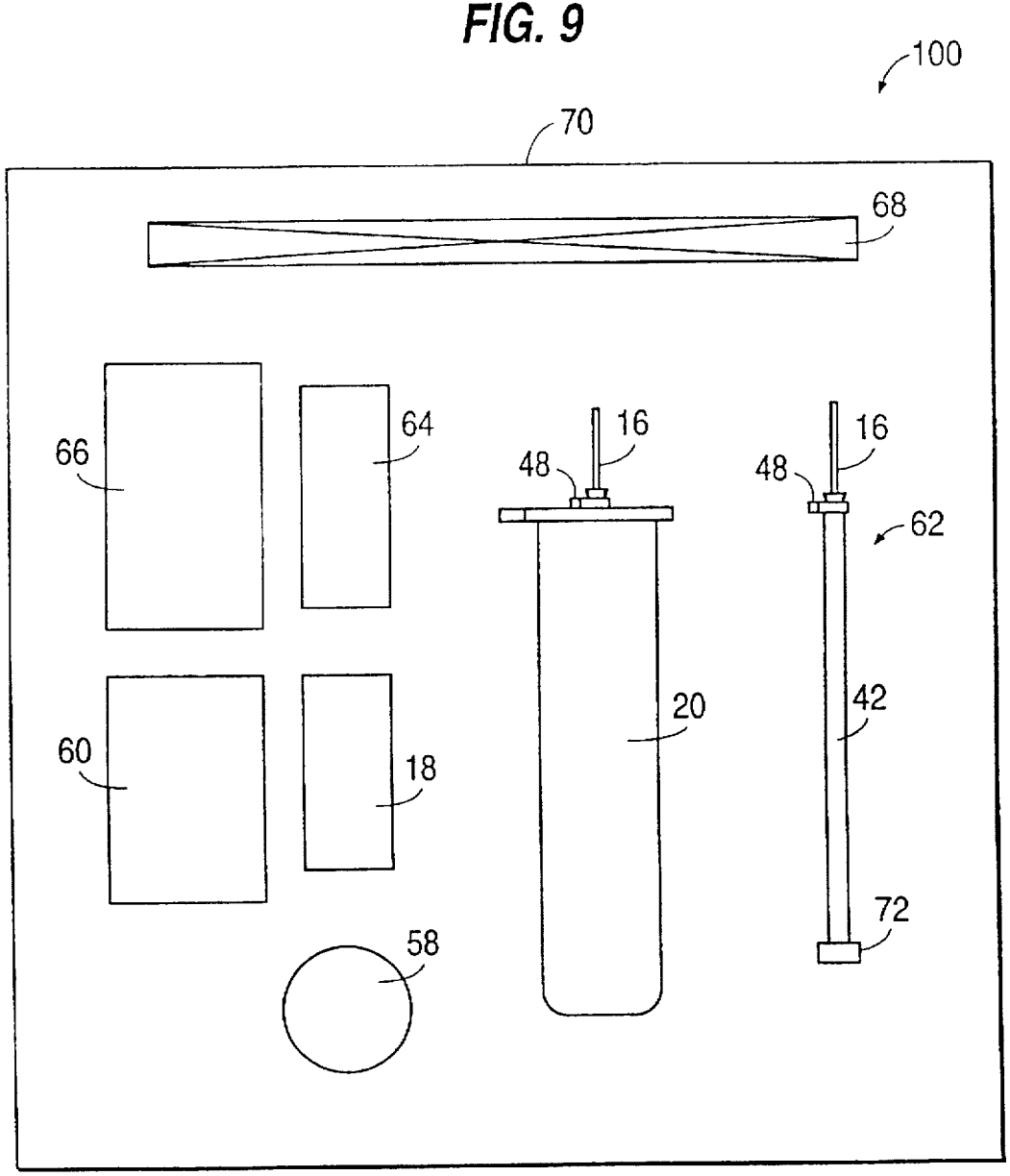
FIG. 9 is a top view of a Pap smear test kit constructed in accordance with a preferred embodiment of the present invention.

After removal of the swab sleeve assembly from the insert tube, the swab (14) is then pushed out of the swab sleeve (42) by the stem (16), and the sample is transferred onto slide (18), which is shown in FIG. 9 as part of a test kit 100. The slide (18) may be a conventional glass slide of the type conventionally used to fix samples for Pap smear tests. The cell sample may be preserved and fixed on the slide (18) by a suitable fixing medium (58), such as a spray or liquid commercially available for fixing cervical samples. The slide (18) may then be stored in an air-tight plastic container (60) for shipment to a clinic or laboratory for analysis. If a second sampling is desired, as discussed further below, it is preferable to proceed with obtaining the second sampling before transferring the first sampling onto the slide (18). In this manner, the user can complete the sampling procedures and then continue with preparing both samples for laboratory analysis.

The present invention allows two samples to be taken by two different swabs, if desired, by allowing the insert tube (20) to remain in the vagina for a second sampling procedure. Thus, after the first swab assembly (40) is removed, a second swab assembly (62) is installed into the guide tube (22) for a second Pap smear. Advantageously, the insert tube (20) may remain in the vagina for both of the Pap smears and therefore does not have to be reinserted or repositioned to obtain the second sample. The second sample is obtained in the same manner as described above for the first sample, and then the second sample is transferred onto a second glass slide (64), fixed by the fixing medium (58), and stored in a second air tight container (66). The two containers (60), (66), with the two samples may then be mailed or otherwise delivered within a suitable shipping envelope (68) or other suitable package to a laboratory or clinic for analysis.

In the illustrated embodiment of the invention, the first and second swab sleeve assemblies (40), (62) are structurally identical to each other. By constructing the swab sleeve assemblies (40), (62) of the same material and to the same dimensions, the total costs of manufacturing the assemblies (40), (62) may be kept to a minimum. Also, by providing the assemblies (40), (62) with identical structures, the system may be used more reliably and with greater confidence by a user with no medical training.

In a preferred embodiment of the invention, all of the components discussed above are packaged in test kit (100) within a single box (70) or other suitable enclosure. In this manner, the test kit will be easily handled by retailers and consumers, and the enclosure (70) will maintain the sterility of the various components of the kit. In a preferred embodiment of the invention, a cover or end cap (72) is provided for maintaining the sterility of the second swab prior to use.

An advantageous feature of the present invention is that the dimensions of the swab assemblies are much less than those of the insert tube (20). As a result, the overall size and total cost of the kit are reduced. In the illustrated embodiment, the outer diameter of the swab sleeve (42) is no more than about 0.25 inch (no more than approximately 0.5 centimeter).

While the invention has been described with reference to specific embodiments, it will be apparent to those skilled in the art that many alternatives, modifications and variations may be made. Accordingly, it is intended to embrace all such alternatives, modifications and variations that may fall within the spirit and scope of the appended claims.

I claim:

1. A cervical sampling device, comprising:

a vaginal insert tube;

a guide sleeve located within said vaginal insert tube;

a swab sleeve located within said guide sleeve, said swab sleeve being removable from said guide sleeve;

a swab for obtaining a cervical sample, said swab being positionable within said swab sleeve in a retracted position; and a stem for pushing said swab out of said swab sleeve to an extended position and into contact with cervical tissue;

wherein said swab sleeve includes rotatable aligning means further including an offset portion for aligning said swab sleeve and said stem in the retracted position in a proper orientation for said swab to obtain a sample of cervical tissue when said swab is positioned in the extended position.

2. The cervical sampling device of claim 1, wherein said insert tube has a rear end and includes a radially extending flange, said flange being located at said rear end of said insert tube.

3. The cervical sampling device of claim 2, wherein said insert tube further includes a handle for manipulating said insert tube, said handle being located at said rear end as an extension of said radial flange.

4. The cervical sampling device of claim 1, further comprising at least two spacers for rigidly supporting said guide sleeve within said insert tube.

5. The cervical sampling device of claim 1, wherein said stem includes a bending portion such that said stem is bent at an angle of approximately 5 degrees when said swab is pushed out of said tubular swab sleeve into said extended position.

6. The cervical sampling device of claim 5, wherein said stem includes a stop member for resisting movement of said stem with respect to said swab sleeve.

7. The cervical sampling device of claim 1, wherein said offset portion includes a handle extending from a radially extending flange on said swab sleeve, said handle being positioned in an upwardly extending direction aligning said stem and said swab in said proper orientation.

8. The cervical sampling device of claim 1 wherein said swab includes a brush portion, said brush portion being in a closed position within said swab sleeve when said swab is in said retracted position and said brush portion expanding to an open position when said swab is pushed out of said swab sleeve into said extended position.

9. The cervical sampling device of claim 1 wherein said swab sleeve, said swab and said stem comprise a first swab sleeve, a first swab and a first stem, said first swab sleeve being removed from said guide sleeve and further comprising a second swab sleeve positionable within said guide sleeve, a second swab located within said second swab sleeve for obtaining a second cervical sample and being positionable within said second swab sleeve in a retracted position, and a second stem for pushing said second swab out of said second swab sleeve into an extended position and into contact with cervical tissue.

10. A Pap smear test system, comprising:

(A) a test system enclosure;

(B) a cervical sampling apparatus disposed within said system enclosure, said sampling apparatus including:

a vaginal insert tube;

a first swab assembly removably positioned within said insert tube; and a second swab assembly disposed within said system enclosure;

wherein each said swab assembly includes a swab sleeve positionable within and removable from said insert tube; a swab for obtaining a cervical tissue sample, each said swab being positionable within said swab sleeve in a retracted position; and a stem for pushing each said swab out of each said swab sleeve to an extended position and into contact with cervical tissue;

and wherein each said swab sleeve includes rotatable aligning means further including an offset portion for aligning said swab sleeve and said stem in the retracted position in a proper orientation for said swab to obtain a sample of cervical tissue when said swab is positioned in the extended position;

(D) first and second slides for receiving said first and second samples from said first and second swabs, respectively; and (E) packaging for transporting one or more of said slides to a different location;

wherein said insert tube, said cervical sampling apparatus, said first and second slides, and said packaging are all disposed within said test system enclosure.

11. The system of claim 10, further comprising first and second containers for receiving said first and second slides, respectively, said containers being disposed within said test system enclosure.

12. The system of claim 10, further comprising fixing means for fixing said cervical tissue samples on said slides, said fixing means being disposed within said test system enclosure.

13. The system of claim 10, further comprising an end cover for preserving the sterility of said second swab, said end cover being located on said second swab sleeve.

14. The system of claim 10, further comprising a tubular guide sleeve for slidably supporting said first and second swab sleeves, said guide sleeve being located within said vaginal insert tube.

15. The system of claim 10, wherein each said stem includes a bending portion such that each said stem is bent at an angle of approximately five degrees when said swab is pushed out of said swab sleeve into said extended position.

16. The system of claim 10, wherein each said stem includes a resilient collar for resisting movement of said stem with relative to said respective swab sleeve.

17. A method for obtaining a cervical tissue sample, said method comprising:

providing a cervical sampling apparatus including a vaginal insert tube and a first swab assembly, the first swab assembly including a first swab sleeve removably positioned within said insert tube, a first swab for obtaining a first cervical tissue sample, the first swab being positioned within the first swab sleeve in a retracted position, and a first stem for pushing the first swab out of the first swab sleeve to an extended position and into contact with cervical tissue;

providing a second swab assembly including a second swab sleeve removably positionable within the insert tube, a second swab for obtaining a second cervical tissue sample, the second swab being positioned within the second swab sleeve in a retracted position, and a second stem for pushing the second swab out of the second swab sleeve to an extended position and into contact with cervical tissue;

each said swab sleeve includes rotatable aligning means further including an offset portion for aligning said swab sleeve and said stem in the retracted position in a proper orientation for said swab to obtain a sample of cervical tissue when said swab is positioned in the extended position;

inserting the vaginal insert tube including the first swab assembly into a vaginal cavity;

applying pressure to the first stem and thereby extending the first swab from the retracted position within the first swab sleeve into the extended position and contacting cervical tissue;

absorbing the first cervical tissue sample into the first swab;

withdrawing the first stem and thereby retracting the first swab into the first swab sleeve;

removing the first swab assembly from the vaginal insert tube while maintaining the position of the vaginal insert tube within the vaginal cavity;

inserting the second swab assembly into the vaginal insert tube;

applying pressure to the second stem and thereby extending the second swab from the retracted position within the second swab sleeve into the extended position and contacting cervical tissue;

absorbing the second cervical tissue sample into the second swab;

withdrawing the second stem and thereby retracting the second swab into the second swab sleeve;

removing the second swab assembly from the vaginal insert tube;

removing the vaginal insert tube from the vaginal cavity; and fixing the first and second cervical tissue samples onto first and second slides.

18. The method of claim 14, further comprising sealing the first and second slides in at least one container, packaging the at least one container for transport, and transporting the at least one container to a different location for analysis.

19. The method of claim 17, further comprising providing a guide sleeve within the vaginal insert tube, the guide sleeve slidably supporting the first and second swab sleeves during the removal thereof.

20. A cervical sampling device, comprising:

a vaginal insert tube;

a guide sleeve located within said vaginal insert tube, said guide sleeve being fixedly supported within said vaginal insert tube by at least two support elements;

a swab sleeve located within said guide sleeve, said swab sleeve being removable from said guide sleeve;

a swab for obtaining a cervical sample, said swab being positionable within said swab sleeve in a retracted position; and a stem for pushing said swab out of said swab sleeve to an extended position and into contact with cervical tissue;

wherein said swab sleeve includes rotatable aligning means further including an offset portion for aligning said swab sleeve and said stem in the retracted position in a proper orientation for said swab to obtain a sample of cervical tissue when said swab is positioned in the extended position.

* * * * *